(12) United States Patent
Shimokawa et al.

(10) Patent No.: US 11,287,431 B2
(45) Date of Patent: Mar. 29, 2022

(54) METHOD OF TESTING FOR PULMONARY HYPERTENSION

(71) Applicant: TOHOKU UNIVERSITY, Miyagi (JP)

(72) Inventors: Hiroaki Shimokawa, Miyagi (JP); Kimio Satoh, Miyagi (JP); Nobuhiro Kikuchi, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 414 days.

(21) Appl. No.: 16/192,042

(22) Filed: Nov. 15, 2018

(65) Prior Publication Data

US 2019/0086427 A1 Mar. 21, 2019

Related U.S. Application Data

(62) Division of application No. 15/305,879, filed as application No. PCT/JP2015/060198 on Mar. 31, 2015, now abandoned.

(30) Foreign Application Priority Data

Apr. 22, 2014 (JP) ................................ 2014-088531

(51) Int. Cl.
  *G01N 33/53* (2006.01)
  *G01N 33/68* (2006.01)

(52) U.S. Cl.
  CPC ......... *G01N 33/6893* (2013.01); *G01N 33/68* (2013.01); *G01N 2333/47* (2013.01); *G01N 2800/12* (2013.01)

(58) Field of Classification Search
  CPC ............... G01N 33/6893; G01N 33/68; G01N 2333/47; G01N 2800/12
  See application file for complete search history.

(56) References Cited

U.S. PATENT DOCUMENTS

| 9,651,563 B2 * | 5/2017 | Jacobs ................ G01N 33/6893 |
| 2003/0175736 A1 * | 9/2003 | Chinnaiyan .......... C12Q 1/6886 435/6.14 |
| 2005/0101608 A1 * | 5/2005 | Santel .................... A61K 45/06 514/252.16 |
| 2011/0212470 A1 | 9/2011 | Somers | |

FOREIGN PATENT DOCUMENTS

| CA | 2447601 | 5/2002 | | |
| JP | 2003-26598 | 1/2003 | | |
| JP | 2010-539449 | 12/2010 | | |
| WO | 03/047591 | 6/2003 | | |
| WO | 2008/013324 | 1/2008 | | |
| WO | 2009/034122 | 3/2009 | | |
| WO | WO-2012076553 A2 * | 6/2012 | ........... | G01N 33/689 |
| WO | WO-2012174294 A1 * | 12/2012 | ........... | C12Q 1/6883 |

OTHER PUBLICATIONS

Burk et al;2005;Annu.Rev.Nutr. 25:215-35, see pp. 219-220.*
Saito et al (Journal of Health sciences, 2001;47(4) 346-352).*
Xia et al (Am. J Clin Nutr 2010;92:525-31).*
Hargreaves et al. (PLOS ONE,2014;vol. 9 issue 1 e84972-e84972).*
Stampher et al., Circulation 2004, 1909:IV3-IV-5, table 2).*
Behr et al. (Eur Respir J 2008;31:1357-1367.*
Mayeux et al. ("Biomarkers: Potential uses and Limitations"; NeuroRx (2004); vol. 1, pp. 182-188).*
International Search Report dated Jun. 23, 2015 in International (PCT) Application No. PCT/JP2015/060198.
Kyotani,, "Primary pulmonary hypertension", Japanese Journal of Clinical Medicine, vol. 59, No. 6, 2001, pp. 1159-1163, with English abstract.
Guidelines for Treatment of Pulmonary Hypertension, 2012(revised), pp. 1-69, cited in the Specification.
Barst et al., "Updated Evidence-Based Treatment Algorithm in Pulmonary Arterial Hypertension", Journal of the American College of Cardiology, vol. 54, No. 1, Jun. 30, 2009, pp. S78-S84.
McLaughlin et al., "A Report of the American College of Cardiology Foundation Task Force on Expert Consensus Documents and the American Heart Association", Circulation, vol. 119, Apr. 28, 2009, pp. 2250-2294.
Galie et al., "Guidelines for the diagnosis and treatment of pulmonary hypertension—The Task Force for the Diagnosis and Treatment of Pulmonary Hypertension of the European Society of Cardiology (ESC) and the European Respiratory Society (ERS), endorsed by the International Society of Heart and Lung Transplantation (ISHLT)", European Heart Journal, vol. 30, 2009, pp. 2493-2537.
Galie et al., "Guidelines for the diagnosis and treatment of pulmonary hypertension—The Task Force for the Diagnosis and Treatment of Pulmonary Hypertension of the European Society of Cardiology (ESC) and the European Respiratory Society (ERS), endorsed by the International Society of Heart and Lung Transplantation (ISHLT)", European Respiratory Journal, vol. 34, No. 6, 2009, pp. 1219-1263.
Misu et al., "A Liver-Derived Secretory Protein, Selenoprotein P, Causes Insulin Resistance", Cell Metabolism, vol. 12, Nov. 3, 2010, pp. 483-495
Simonneau et al., "Updated Clinical Classification of Pulmonary Hypertension", Journal of the American College of Cardiology, vol. 62, No. 25, Dec. 24, 2013, pp. D34-D41.
Saito et al., (Journal of Health Science, 47(4) 346-352 (2001).
Cusbio Elisa Kit (2013;, retrieved from https://www.cusabio.com/uploadfile/Ins/2018-01-22/CSB-EL021018HU.pdf).
Idexx Elisa technical Guide 2010, retrieved from http://www.idexx.com.tw/pdf/zh_tw/livestock-poultry/elisa-technical-guide.pdf.
Rodrigo et al., "The role of oxidative stress in the pathophysiology of hypertension", Hypertension Research, 2011, vol. 34, No. 4, pp. 431-441.

(Continued)

*Primary Examiner* — Carmencita M Belei
(74) *Attorney, Agent, or Firm* — Wenderoth, Lind & Ponack, L.L.P.

(57) ABSTRACT

A primary object of the present invention is to provide a method for conveniently and accurately testing for pulmonary hypertension. To achieve this object, the present invention provides a method for testing for pulmonary hypertension using as an indicator the concentration of selenoprotein P protein in a sample derived from a subject.

2 Claims, 4 Drawing Sheets

(56) References Cited

OTHER PUBLICATIONS

Strauss et al., "*SEPP 1* gene variants and abdominal aortic aneurysm: gene association in relation to metabolic risk factors and peripheral arterial disease coexistence", Scientific Reports, 2017, vol. 4, No. 1, pp. 1-7.

Kikuchi et al., "Selenoprotein p promotes vascular smooth muscle cell proliferation and pulmonary hypertension—a possible novel therapeutic target", European Heart Journal, 2015, vol. 36, No. Suppl. 1, p. 1206 (2 pages).

Extended European Search Report dated Oct. 2, 2017 in European Patent Application No. 15782732.0.

Communication pursuant to Article 94(3) EPC dated May 24, 2018 in corresponding EP application No. 15782732.0.

Yang et al., "Serum Selenoprotein P Levels in Patients with Type 2 Diabetes and Prediabetes: Implications for Insulin Resistance, Inflammation, and Atherosclerosis", Journal of Clinical Endocrinology and Metabolism, vol. 96, No. 8, 2011, pp. E1325-E1329.

Hill et al., "Selenoprotein P Concentration in Plasma is an Index of Selenium Status in Selenium-Deficient and Selenium-Supplemented Chinese Subjects", The Journal of Nutrition, vol. 126, No. 1, 1996, pp. 138-145.

Yang et al., "Purification and Quantitation of a Rat Plasma Selenoprotein Distinct from Glutathione Peroxidase Using Monoclonal Antibodies", Journal of Biological Chemistry, vol. 262, No. 27, 1987, p. 13372-13376.

Hollenbach, et al., "New assay for the measurement of selenoprotein P as a sepsis biomarker from serum", Journal of Trace Elements in Medicine and Biology, vol. 22, No. 1, 2008, pp. 24-32.

\* cited by examiner

METHOD OF TESTING FOR PULMONARY HYPERTENSION

TECHNICAL FIELD

The present invention mainly relates to a method of testing for pulmonary hypertension. The present invention further relates to a biomarker for detecting pulmonary hypertension, and a test kit for pulmonary hypertension.

BACKGROUND ART

Pulmonary hypertension is a disease in which pulmonary artery blood pressure is increased due to a variety of causes. According to WHO classification or the like, pulmonary hypertension is classified into pulmonary arterial hypertension (PAH), pulmonary hypertension due to left heart disease, pulmonary hypertension due to lung disease and/or hypoxia, chronic thromboembolic pulmonary hypertension (CTEPH)), and pulmonary hypertension of unknown cause due to a combination of factors (Non-patent Literature (NPL) 1 to 5). In Japan, pulmonary hypertension includes many diseases designated as intractable diseases (specified diseases). In the case of patients at the terminal stage, lung transplantation may be necessary.

For example, in pulmonary arterial hypertension, pulmonary artery blood pressure abnormally increases due to stenosis of distal pulmonary arteries. Abnormal growth and denaturation of endothelial cells and vascular smooth muscle cells are considered to cause stenosis of distal pulmonary arteries. Pulmonary arterial hypertension is a lethal disease with a five-year survival rate of 20% in untreated patients. Early diagnosis is difficult, even for cardiologists. When diagnosed, patients are often already at the terminal stage. Although there are still no means other than lung transplantation for saving critically ill patients, the number of donors is limited, and there are many cases in which patients die while awaiting transplantation. The disease advances quickly in many younger-age cases, and death due to right heart failure frequently occurs, even when multidrug therapy is used. In recent years, there has been an increase in the number of pulmonary hypertension patients in Japan. However, the causes of this disease have yet to be fully clarified.

With the progression of therapeutic methods in recent years, if pulmonary hypertension can be accurately diagnosed, sufficient therapeutic effects can be expected. In particular, if the disease is found early, therapeutic effects as well as prognostic improvement can be expected. For example, if pulmonary arterial hypertension is found at an early stage and an appropriate procedure is performed, the five-year survival rate is about 50%.

However, subjective symptoms in the early stage of pulmonary hypertension patients are limited to nonspecific symptoms, such as shortness of breath during exertion, and fatigue. Therefore, doctors must determine, mainly through medical interviews, the probability that the patient has pulmonary hypertension. Furthermore, to accurately test for pulmonary hypertension, right heart catheterization, lung ventilation-blood flow scintigraphy, chest imaging CT, and like tests must be performed. Specifically, hospitalization is necessary to perform pulmonary hypertension tests, thus imposing a great burden on both patients and health care providers.

Under such circumstances, there has been desired a method for easy and accurate testing for pulmonary hypertension, the method being performed on an outpatient basis by blood sampling or the like mainly for the purpose of screening.

Selenoprotein P protein is one of the Se-containing proteins (a member of the selenoprotein family), and is a protein containing multiple selenocysteine residues. It has also been found that selenoprotein P protein is one of the causes of insulin resistance in type 2 diabetes, and that extracellular stimulation of selenoprotein P protein suppresses intracellular AMPK activity in hepatocytes (NPL 6). However, selenoprotein P protein, including its signaling pathway, remains largely unknown.

CITATION LIST

NPL

NPL 1: The Japanese Circulation Society: Pulmonary Hypertension Treatment Guidelines (revised 2012)
NPL 2: J Am Col Cardiol, 2009; 54 (suppl): S78-84
NPL 3: Circulation, 2009; 119: 2250-2294
NPL 4: Eur Heart J, 2009; 30: 2493-2537
NPL 5: Euro Respir J, 2009; 34: 1219-1263
NPL 6: Cell Metabolism, 2010; 12: 483-495
NPL 7: J Am Col Cardiol, 2013; 62 (25 suppl): D34-41

SUMMARY OF INVENTION

Technical Problem

A main object of the present invention is to provide a method of testing for pulmonary hypertension, and, in particular, a method capable of easily and accurately testing for pulmonary hypertension. The present invention further relates to a biomarker for detecting pulmonary hypertension, and a test kit for pulmonary hypertension.

Solution to Problem

The present inventors conducted extensive research to achieve the above. As a result, the inventor found that pulmonary hypertension can be tested by using as an indicator the concentration of selenoprotein P protein in a sample derived from a subject. The present invention has been accomplished through further research based on this finding.

Specifically, the present invention includes the following.

Item 1: A method of testing for pulmonary hypertension comprising performing a test for pulmonary hypertension using as an indicator the concentration of selenoprotein P protein in a sample derived from a subject.

Item 2: The method according to claim 1 comprising:
[1] measuring the concentration of selenoprotein P protein in a sample derived from a subject; and
[2] assessing the presence or absence of pulmonary hypertension and/or the risk of pulmonary hypertension, based on the results obtained in [1].

Item 3: The method according to claim 2, wherein when the concentration of selenoprotein P protein is higher than a predetermined cutoff value, the subject is assessed as having pulmonary hypertension and/or as being at risk for developing pulmonary hypertension.

Item 4: The method according to any one of claims 1 to 3, wherein the sample derived from a subject is plasma.

Item 5: A biomarker for detecting pulmonary hypertension, comprising selenoprotein P protein.

Item 6: A test kit for pulmonary hypertension, comprising a means for measuring the concentration of selenoprotein P protein in a sample derived from a subject.

Item 7: A method for treating pulmonary hypertension comprising the steps of:
(i) testing for pulmonary hypertension using as an indicator the concentration of selenoprotein P protein in a sample derived from a subject; and
(ii) subjecting a subject in which pulmonary hypertension is detected to a procedure for treating pulmonary hypertension and/or preventing progression of pulmonary hypertension.

Advantageous Effects of Invention

The present invention provides a method for easily and accurately testing for pulmonary hypertension. Because, for example, the testing method of the present invention can be performed by testing patients' blood, and can be performed on an outpatient basis, little burden is imposed on both patients and health care providers.

The testing method of the present invention is expected to allow pulmonary hypertension patients to be proactively tested, and thus receive effective therapy early.

BRIEF DESCRIPTION OF DRAWINGS

FIG. 2 shows the results of four independent trials under each of the following conditions: at normoxia; at hypoxia; and at hypoxia in the presence of fasudil (hypoxia+fasudil). In FIG. 2, the upper column shows the detection of selenoprotein P protein in whole cell lysates by western blot analysis, whereas the lower column shows the detection of selenoprotein P protein in conditioned medium by western blot analysis.

DESCRIPTION OF EMBODIMENTS

Figure 1:
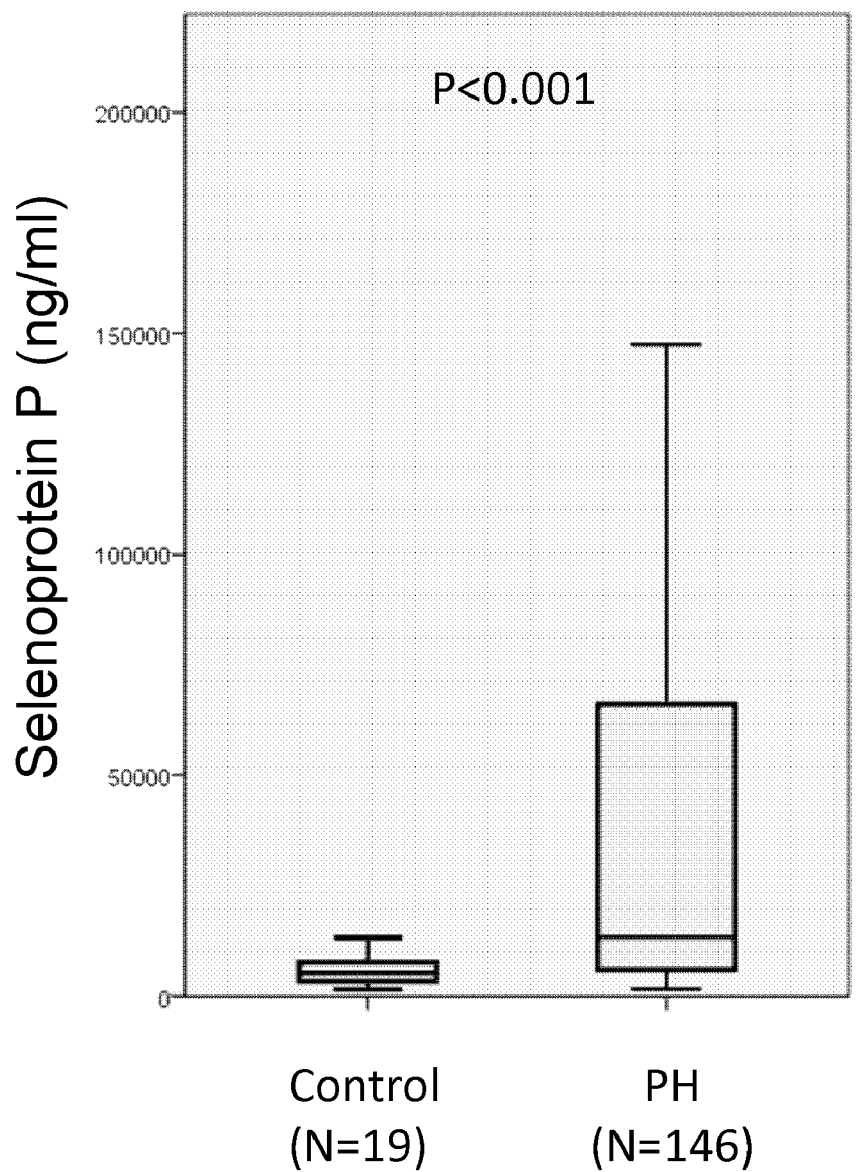
FIG. 1 shows the results of measuring the plasma concentration of selenoprotein P protein in pulmonary hypertension patients (PH, N=146) and control patients (Control, N=19), which are shown in a box plot. The plasma concentration (ng/ml) of selenoprotein P protein in pulmonary hypertension patients increased. $P<0.001$

1. Method of Testing for Pulmonary Hypertension Pulmonary Hypertension

The testing method of the present invention is to test for pulmonary hypertension.

Pulmonary hypertension includes diseases in which increased pulmonary arterial pressure (mPAP, for example, 25 mmHg or more) is observed as a clinical observation. Pulmonary hypertension include pulmonary arterial hypertension (PAH), pulmonary hypertension due to left heart disease, pulmonary hypertension due to lung disease and/or hypoxia, chronic thromboembolic pulmonary hypertension (CTEPH), other pulmonary hypertension of unknown cause due to a combination of factors, and the like.

An example of a pathological condition of pulmonary hypertension is pulmonary arterial hypertension. Examples of significant clinical observations of pulmonary arterial hypertension include increased pulmonary artery pressure (mPAP, for example, 25 mmHg or more) and normal pulmonary wedge pressure (right atrial pressure) (PCWP, for example, 15 mmHg or less) (these can be measured, for example, by right heart catheterization); pulmonary blood flow distribution anomalies are not observed (these can be measured by, for example, lung ventilation-blood flow scintigraphy).

Pulmonary arterial hypertension is a lethal disease in which blood vessel endothelial function deterioration, vascular smooth muscle cell growth, inflammatory cell infiltration, etc., have a complex interplay in the progression of wall-thickening or narrowing of pulmonary microvessels (pulmonary vascular remodeling). Its early diagnosis is difficult, even for cardiologists. When introduced to an institution for lung transplantation, patients are often already at the terminal stage. Although there are still no means other than lung transplantation for saving critically ill patients, the number of donors is limited, and there are many cases in which patients die while awaiting transplantation. Among these, the disease advances quickly in many idiopathic pulmonary arterial hypertension patients (Idiopathic PAH, IPAH), and shows advanced pulmonary artery remodeling characterized by abnormal growth of pulmonary artery vascular smooth muscle cells. Therefore, control of right heart failure is difficult, even with multidrug therapy, and there are still many cases in which patients die at a young age. Accordingly, early diagnosis and treatment are necessary before the clinical stage advances.

Pulmonary arterial hypertension includes pathological conditions such as idiopathic pulmonary arterial hypertension (IPAH)), heritable pulmonary arterial hypertension, drug/poison-induced pulmonary arterial hypertension, pulmonary arterial hypertension associated with other pathological conditions, persistent pulmonary hypertension of newborns, connective tissue disease, portopulmonary hypertension (portoPH), congenital heart diseases (shunt PAH), and the like.

Pathological conditions of pulmonary hypertension other than pulmonary arterial hypertension are also known. Specifically, reference can be made to guidelines in Japan (NPL 1), guidelines in Europe and America (NPL 2 to 5), etc.

The 2013 Nice Conference redefined pulmonary hypertension, and reclassified clinical classification (in this specification, this is referred to as "Nice Classification") (NPL 1, NPL 7).

Testing Method

The testing method of the present invention uses as an indicator the concentration of selenoprotein P protein in a sample derived from a subject.

"Testing" as used herein includes testing for the presence or absence of pulmonary hypertension and testing for the risk of pulmonary hypertension. Preferably, "testing" refers to testing for the presence or absence of pulmonary hypertension. "Testing for the risk" includes testing and determination of the presence or absence of a probability of developing pulmonary hypertension in the future. "Testing" can be paraphrased as "determination" or "diagnosis."

Sample and Subject

In the testing method of the present invention, the sample is obtained from a subject.

The sample is derived from a subject to be tested by the testing method. The subject is not particularly limited, and examples thereof include mammals including humans. Examples of non-human mammals include mice, rats, dogs, cats, cattle, sheep, horses, and the like. The subject of the testing method of the present invention is preferably a human. When the subject is a human, examples of subjects include patients having any subjective symptom that is characteristic of pulmonary hypertension, such as shortness of breath during exertion, or chest discomfort, and preferably patients suspected to have pulmonary hypertension.

When the subject is a human, the sex, age, and race of the subject are not particularly limited. In a preferable embodiment of the present invention, the subject is an Asian person (e.g., Japanese, Chinese, or South Korean) and is particularly preferably Japanese. In one preferable embodiment of the present invention, the subject is female in view of a statistically larger number of patients.

The sample is preferably a blood sample derived from the subject. Specific examples of the blood sample include blood (whole blood), blood-derived serum and plasma, and the like. The blood sample is preferably plasma. Plasma is a part of blood obtained by removing corpuscular components from blood. For example, it can be obtained as a supernatant when subjected to centrifugal separation under conditions in which blood is not solidified (for example, in the presence of sodium citrate).

The blood vessel from which the blood sample is derived is not limited. The blood can be collected from a systemic circulation blood vessel (arteries (peripheral arteries), veins (peripheral veins), and capillaries) or a pulmonary circulation blood vessel (pulmonary arteries, pulmonary veins, and pulmonary capillaries). From the viewpoint of collecting blood easily, it is preferable that the blood is collected from a systemic circulation blood vessel, in particular, from a vein (peripheral vein). Blood can be collected from a pulmonary circulation blood vessel upon right heart catheterization.

The testing method of the present invention preferably comprises the steps of:
[1] measuring the concentration of selenoprotein P protein in a sample derived from a subject; and
[2] assessing the presence and/or absence of pulmonary hypertension or the risk of pulmonary hypertension, based on the results obtained in [1] above.

Concentration of Selenoprotein P Protein in Sample

In the testing method of the present invention, the concentration of selenoprotein P (SeP) protein in a sample is used as an indicator.

Selenoprotein P protein is a known protein.

Human selenoprotein P protein is one of the Se-containing proteins (a member of selenoprotein family) encoded on the selenoprotein P, plasma, 1 (SEPP1) gene locus, and is a protein containing multiple selenocysteine residues. Selenoprotein P protein is known to mainly secrete from the liver extracellularly. The "P" in the term refers to "plasma."

Selenoprotein P protein is known to be a cause of insulin resistance in type 2 diabetes mellitus. It has also been found that extracellular stimulation of selenoprotein P protein suppresses intracellular AMPK activity in hepatocytes (NPL 6). However, selenoprotein P protein, including its signaling pathway, remains largely unknown. In particular, selenoprotein P protein's involvement in pulmonary hypertension is unknown.

For example, the amino acid sequences of human (*Homo sapiens*) selenoprotein P protein and mouse (*Mus musculus*) selenoprotein P protein, as well as the amino acid sequences of mRNA encoding these proteins, have been registered at GenBank provided by the National Center for Biotechnology Information (NCBI), under the following accession numbers (it should be understood that when multiple revisions have been registered, each number refers to the latest revision):

Human selenoprotein P Proteins: NP_005401, NP_001078955, NP_001087195;
Human selenoprotein P mRNA: NM_005410, NM_001085486, NM_001093726;
Mouse selenoprotein P Proteins: NP_033181, NP_001036078, NP_001036079; and
Mouse selenoprotein P mRNA: NM_009155, NM_001042613, NM_001042614.

The means for measuring the blood concentration of selenoprotein P protein can be suitably selected by persons skilled in the art. Examples of preferable means include immunoassay using an antibody specifically detecting selenoprotein P protein (i.e., an antibody specifically binding to selenoprotein P protein) (including full length of antibody (immunoglobulin protein) molecules and fragments such as F(ab) and F(ab')$_2$). Examples of immunoassay include ELISA, EIA, western blot, and the like. Among these, techniques that can perform a quantitative test, such as ELISA, are preferable. The antibody that can be used in immunoassay is not particularly limited as long as it can specifically detect selenoprotein P protein in a sample.

The concentration of selenoprotein P protein in a sample can also be measured by using a commercially available reagent. For example, a commercially available product can be used as a reagent for determining the concentration of selenoprotein P protein in a sample. Examples of commercially available products include, but are not limited to, a Human Selenoprotein P, SEPP1 ELISA Kit (produced by Cusabio, Model No.: CSB-EL021018HU). Alternatively, as antibodies for detecting selenoprotein P protein, commercially available antibodies specifically binding to anti-selenoprotein P, such as an anti-selenoprotein P antibody (produced by Santa Cruz Biotechnology, Model No.: sc-30162), can also be used.

The determined concentration of selenoprotein P protein in a sample may be an absolute value and a relative value. Preferably, an absolute value of the selenoprotein P protein concentration in a sample is determined.

Assessment Criteria

In the testing method of the present invention, the presence or absence of and/or the risk of pulmonary hypertension can be assessed, based on the measured concentration of selenoprotein P protein in samples. The assessment criteria for the testing method can be suitably selected by persons skilled in the art.

A predetermined cutoff value can be used as assessment criteria. For example, when the concentration of selenoprotein P protein is used as an indicator, if the concentration of selenoprotein P protein in a sample is higher than a predetermined cutoff value, the patient can be determined to have pulmonary hypertension, or have a probability of developing pulmonary hypertension.

The cutoff value can be determined by various statistical analysis techniques. Examples of the cutoff value include a median or mean value in pulmonary hypertension, a value determined based on ROC curve analysis (e.g., Youden's index), and the like. Multiple cutoff values can also be set.

When the concentration of selenoprotein P protein is used as an indicator, the cutoff value can be set to, for example, about 10 µg/ml. The concentration of selenoprotein P protein in healthy subjects is usually in the range of about 3 to 8 µg/ml.

Other Indicators

The testing method of the present invention may be combined with another known or future testing method for pulmonary hypertension.

In one embodiment of the present invention, the testing method may comprise a step of measuring a tricuspid regurgitation pressure gradient (TRPG) in a subject. The TRPG can be measured by cardiac ultrasonography. The TRPG refers to a difference between a pressure of blood squeezed out of the heart and a pressure of blood having passed through the valve, which can be calculated by echocardiography. In general, when the TRPG is about 50 mmHg or more, the subject can be determined to have a high probability of having pulmonary hypertension. In the testing method according to this embodiment of the present invention, the subject can be determined to have a high probability of having pulmonary hypertension not only when the TRPG is about 50 mmHg or more, but also when the TRPG is about 50 mmHg or less and the measured concentration of selenoprotein P protein in a sample is equal to or higher than a predetermined cutoff value.

Pulmonary hypertension in a subject is thus tested.

The subject determined to have pulmonary hypertension or have a risk of developing pulmonary hypertension by the testing method of the present invention is preferably subjected to a thorough examination of the presence or absence of pulmonary hypertension and/or identification of a lesion by right cardiac catheterization, lung ventilation-blood flow scintigraphy, chest computed tomography (CT), lung arteriography, optical coherence tomography (OCT), or the like.

In particular, the patient determined to have a high probability of having pulmonary hypertension by a thorough examination is preferably subjected to an appropriate procedure for treating and/or preventing progression of pulmonary hypertension. For example, when pulmonary hypertension is pulmonary arterial hypertension, examples of appropriate procedures include administration of endothelin receptor antagonists (e.g., bosentan, ambrisentan), administration of prostaglandin $I_2$ (prostacyclin) preparations, administration of phosphodiesterase-5 (PDE-5) inhibitors (e.g., sildenafil and tadalafil), and the like. These treatments can be used singly, or in a combination of two or more. From the viewpoint of high therapeutic effects, combination therapy, in particular, triple-combination therapy, is preferable.

Although it is unnecessary for a subject who was not assessed as having pulmonary hypertension or as being at risk of developing pulmonary hypertension to receive immediate care, receiving sufficient follow-up is preferable.

2. Kit

The present invention further provides a kit for testing for pulmonary hypertension.

The kit of the present invention includes a means for measuring the concentration of selenoprotein P protein in a sample derived from a subject.

Examples of means for measuring the concentration of selenoprotein P protein include the above-mentioned means for performing immunoassay etc. using an antibody that specifically detects selenoprotein P protein. Specific examples include antibodies that specifically detect selenoprotein P protein and/or other reagents for performing immunoassay, such as ELISA, EIA, or western blot.

The kit of the present invention may further include other components, if necessary. Examples of such other components include, but are not limited to, instruments for collecting a sample (e.g., syringes), positive control samples (e.g., samples derived from patients confirmed to have pulmonary hypertension), negative control samples (e.g., samples derived from patients confirmed not to have pulmonary hypertension (healthy subjects)), and the like. The kit may also include a procedure manual for performing the test method.

The kit of the present invention can be produced by appropriately preparing the above-mentioned components according to a usual method.

Although the usage of the kit is not particularly limited, the kit is preferably used in the testing method described above. When the kit is used in the testing method described above, the testing for pulmonary hypertension can easily be conducted.

3. Method for Treatment

The present invention further provides a method for treating pulmonary hypertension. The "treatment" or "treating" as used herein includes treatments for pulmonary hypertension and maintenance therapies for symptomatic relief and recurrence prevention.

The method for treatment of the present invention comprises the steps of:

(i) testing for pulmonary hypertension using as an indicator the concentration of selenoprotein P protein in a sample derived from a subject; and (ii) subjecting the subject to a treatment for treating pulmonary hypertension and/or preventing progression of pulmonary hypertension.

In step (i), the testing method described in the above-mentioned section "1. Method of Testing for Pulmonary Hypertension" is performed.

Subsequently, the subject in whom pulmonary hypertension was detected is subjected to a treatment for treating pulmonary hypertension and/or preventing progression of pulmonary hypertension (step (ii)).

Between steps (i) and (ii), there may be conducted a thorough examination of the presence or absence of a cardiovascular disease and/or identification of a lesion by a thorough examination, such as cardiac catheterization or angiography (including X-ray angiography, computed tomographic (CT) angiography, and nuclear magnetic resonance (MR) angiography).

As a procedure for treating pulmonary hypertension and/or preventing progression of a cardiovascular disease, a known appropriate procedure is performed. For example, when the pulmonary hypertension is pulmonary arterial hypertension, procedures include, for example, administration of endothelin receptor antagonists (e.g., bosentan, ambrisentan); administration of prostaglandin $I_2$ (prostacyclin) preparations; administration of phosphodiesterase-5 (PDE-5) inhibitors (e.g., sildenafil and tadalafil); and the like. These treatments can be used singly, or in a combination of two or more. From the viewpoint of high therapeutic effects, combination therapy, in particular, triple-combination therapy, is preferable.

Thus, pulmonary hypertension is treated.

EXAMPLES

The present invention is described in more detail below with reference to Examples etc. However, the present invention is not limited to these examples.

The statistical analysis and production of box plots were performed using IBM SPSS statistics.

Example 1: Test for Pulmonary Hypertension

The plasma concentration of selenoprotein P protein in pulmonary hypertension patients and non-pulmonary hypertension patients was measured. The pulmonary hypertension patients as subjects were patients diagnosed as having pulmonary arterial hypertension.

Patient Group

The blood sampled from the following patient groups was subjected to testing.
(i) Non-pulmonary hypertension patient (non-PH) group (control group): 19 persons (a group of healthy subjects who were suspected of having a heart disease and underwent a thorough examination, including cardiac catheterization, and in whom no lesion was observed); and
(ii) a group of pulmonary hypertension (PH) patients: 146 persons.

This research was approved beforehand by the Medical Ethics Committee of Tohoku University, and performed with the informed consent and approval of every patient.

Method

Plasma was separated from peripheral vein-derived blood samples and pulmonary artery-derived blood samples obtained from the above-mentioned patient groups at right heart catheterization. The plasma concentration of selenoprotein P protein was measured by ELISA using a Human Selenoprotein P, SEPP1 ELISA kit (produced by Cusabio Inc.; Model No. CSB-EL021018HU).

Results and Discussion

FIG. 1 shows the results. As shown in FIG. 1, it became clear that pulmonary hypertension patients have a plasma concentration of selenoprotein P protein significantly higher than that of non-pulmonary hypertension patients.

Example 2: Pulmonary Hypertension Test

The plasma concentration of selenoprotein P protein was measured in pulmonary hypertension patients and in non-pulmonary hypertension patients in the same manner as in Example 1.

Patient Group

The blood sampled from the following patient groups was tested.
(i) Non-pulmonary hypertension patient (non-PH) group (control group): 20 persons; and
(ii) pulmonary hypertension patient (PH) group: 183 persons.

The detailed breakdown of the pulmonary hypertension patients is as follows:
connective tissue disease [CPAH; Group 1, 4)-1, Nice Classification]: 25 persons;
chronic thromboembolic pulmonary hypertension [CTEPH; Group 4, Nice Classification]: 51 persons;
idiopathic pulmonary arterial hypertension [IPAH; Group 1, 1, Nice Classification]: 58 persons;
pulmonary hypertension associated with lung diseases and/or hypoxemia [Lung-PAH; Group 3, Nice Classification]: 10 persons;
pulmonary hypertension associated with unknown multifactor mechanisms [non-categorized; Group 5, Nice Classification]: 13 persons;
portopulmonary hypertension [portoPH; Group 1, 4)-3, Nice Classification]: 6 persons; and
congenital heart disease [shunt PAH; Group 1, 4)-4, Nice Classification]: 20 persons.

This research was approved beforehand by the Medical Ethics Committee of Tohoku University, and performed with the informed consent and approval of every patient.

Method

Plasma was separated from the blood samples obtained from the above patient groups in the same manner as in Example 1. The selenoprotein P protein concentration in plasma was measured.

Results and Discussion

Figure 3:
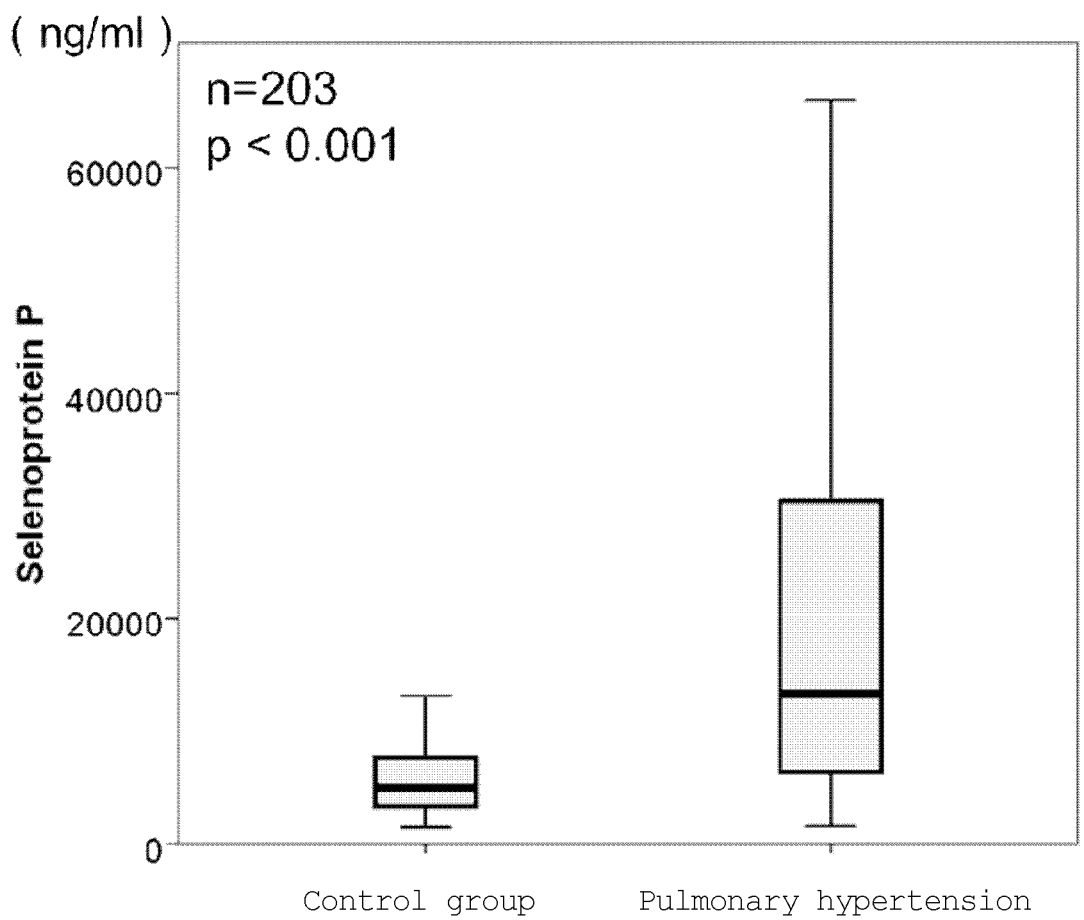
FIG. 3 shows the results of measuring the plasma concentration of selenoprotein P protein in pulmonary hypertension patients (PH, n=203) and control patients (Control, n=20), which are shown in a box plot.
Figure 4:
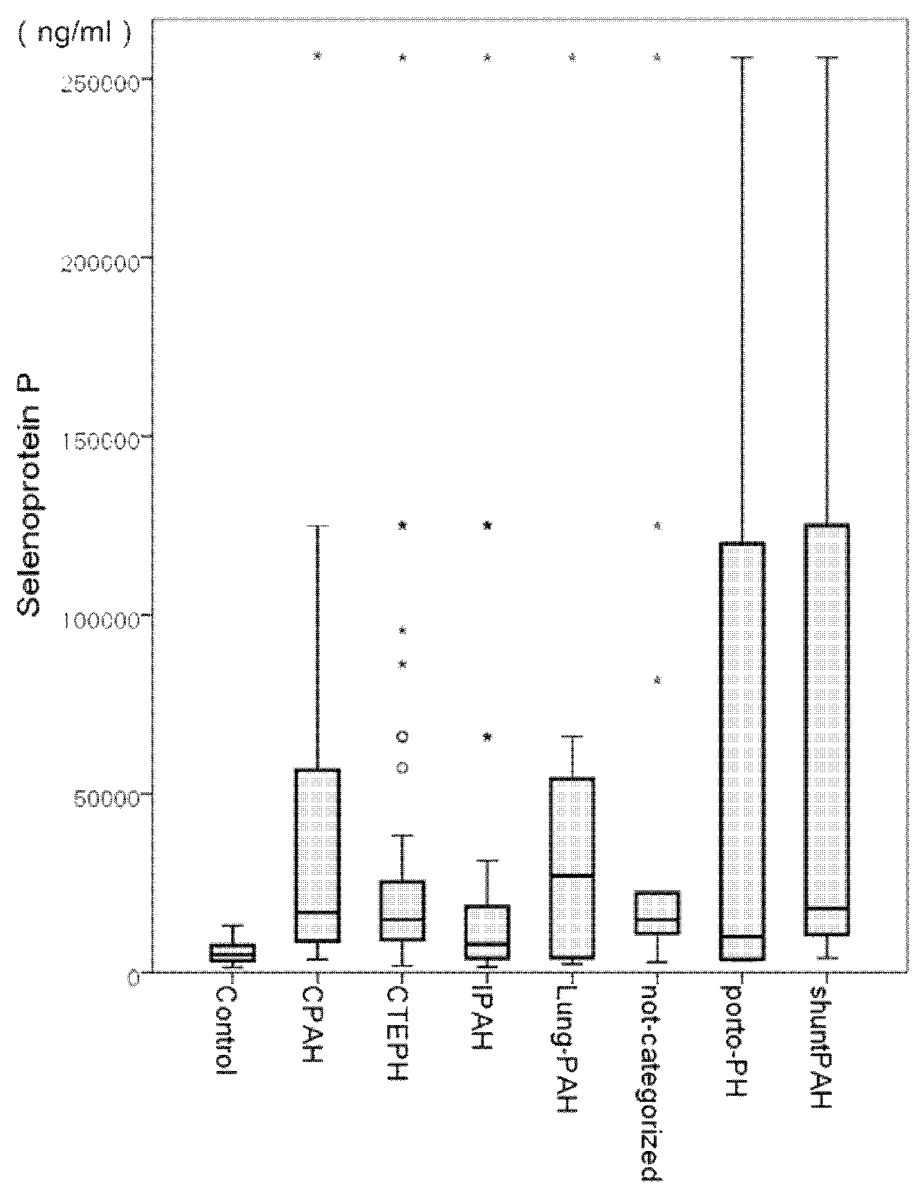
FIG. 4 shows the results of measuring the plasma concentration of selenoprotein P protein in patients with each type of pulmonary hypertension, which are shown in a box plot. The asterisks and circles in FIG. 4 represent the outliers.

FIGS. 3 and 4 show the results. FIG. 3 shows the measurement results of all of the pulmonary hypertension patients. FIG. 4 shows the results of each type of pulmonary hypertension. The results revealed that irrespective of the type of pulmonary hypertension, all types of pulmonary hypertension patients had a significantly higher plasma concentration of selenoprotein P protein than non-pulmonary hypertension patients.

Reference Example 1

The response of pulmonary artery smooth muscle cells (PASMC) in idiopathic pulmonary arterial hypertension (IPAH) patients (hereinafter also referred to as IPAH-PASMC) to hypoxia stimulation was observed.

Material

Primary cell lines were established from pulmonary vascular smooth muscle in idiopathic pulmonary arterial hypertension patients, in accordance with the following document: Ogawa A, Nakamura K, Matsubara H, Fujio H, Ikeda T, Kobayashi K, Miyazaki I, Asanuma M, Miyaji K, Miura D, Kusano K F, Date H, Ohe T, Circulation, 2005; 112: 1806-1812. The pulmonary vascular smooth muscle in idiopathic pulmonary arterial hypertension patients was isolated from pulmonary arteries having an outer diameter of 1.5 mm or less.

Culture Conditions

IPAH-PASMC was cultured in D-MEM medium supplemented by 10% FBS (fetal bovine serum) at 37° C. under constant temperature and constant humidity conditions at 95% air and 5% $CO_2$ in accordance with a usual method. In this test, passage 4 to 7 cells at a confluence of 70 to 80% were used.

Test Method

The cells to be used for the test were cultured for 24 hours under one of the following conditions:
at normoxia (oxygen concentration: 21%);
at hypoxia (oxygen concentration: 2%); and
at hypoxia in the presence of fasudil (hydroxyfasudil concentration: 10 μM).

After culturing, whole cell lysates and a conditioned medium were prepared for each sample, and selenoprotein P protein was detected by western blot analysis.

Results and Discussion

Figure 2:
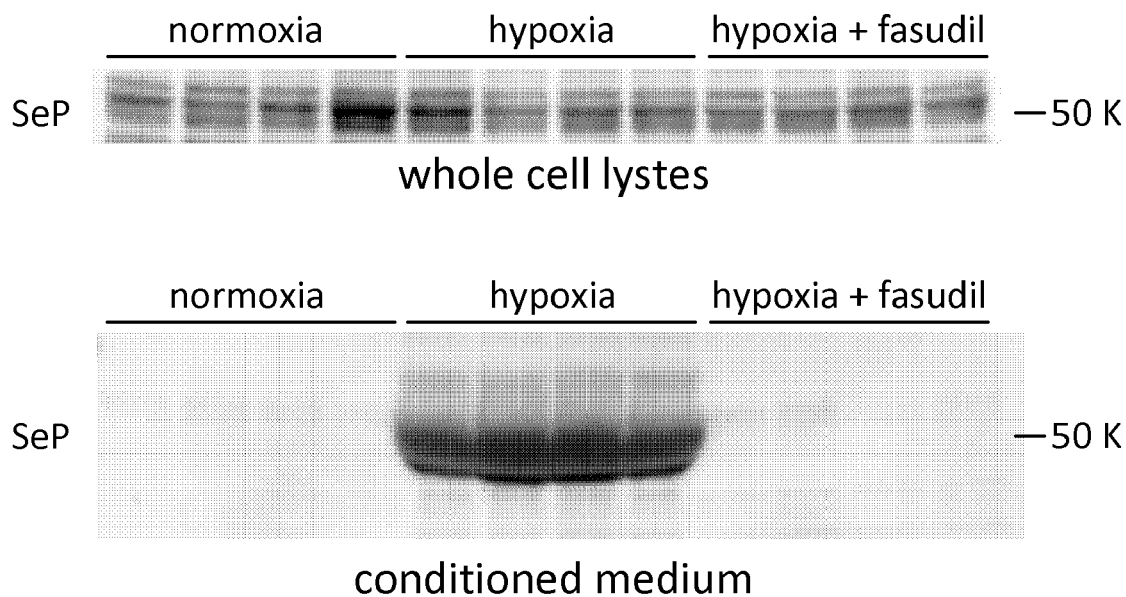
FIG. 2 shows the results of detecting selenoprotein P protein in pulmonary blood vessel smooth muscle cells derived from idiopathic pulmonary arterial hypertension patients.

FIG. 2 shows the results. It became clear that the pulmonary blood vessel smooth muscle cells derived from idiopathic pulmonary arterial hypertension patients promote extracellular secretion of selenoprotein P protein (into the medium) at hypoxia than at normoxia. In the presence of fasudil, which is an inhibitor of Rho kinase (ROCK), enhanced secretion of selenoprotein P protein was not observed, even at hypoxia.

The above experimental results suggest that in the pulmonary artery vascular smooth muscle cells derived from pulmonary arterial hypertension patients, selenoprotein P protein is secreted Rho kinase-dependently by hypoxia stimulation.

The invention claimed is:

1. A method for diagnosing and treating pulmonary hypertension comprising the steps of:
(i) obtaining a blood plasma sample from the a subject suspected of having a pulmonary hypertension, (ii)

measuring the concentration of selenoprotein P protein in the subject's blood plasma sample using an ELISA kit, wherein when the concentration of selenoprotein P protein in the subject's sample is higher than 10μg/ml or above a predetermined cutoff value obtained from a blood sample from healthy subjects indicates the subject has pulmonary hypertension; and (iii) subjecting the subject having pulmonary hypertension to a procedure for treating pulmonary hypertension and/or preventing progression of pulmonary hypertension, wherein the procedure for treating pulmonary hypertension and/or preventing progression of pulmonary hypertension comprises at least one selected from the group consisting of administration of endothelin receptor antagonists, administration of prostaglandin 12 preparations, and administration of phosphodiesterase-5 inhibitors.

2. The method according to claim 1, wherein in step (ii), the measured concentration of selenoprotein P protein in the subject's blood plasma sample is above the predetermined cutoff value obtained from the blood plasma sample from healthy subjects and indicates the subject has pulmonary hypertension.

* * * * *